(12) United States Patent
Kriek

(10) Patent No.: US 6,375,684 B1
(45) Date of Patent: Apr. 23, 2002

(54) HIP PROSTHESIS AND METHOD FOR FITTING SUCH HIP PROSTHESIS

(75) Inventor: Hans Rudolf Kriek, Amsterdam (NL)

(73) Assignee: Novarticulate Holding, Ltd., London (GB)

( * ) Notice: Subject to any disclaimer, the term of this patent is extended or adjusted under 35 U.S.C. 154(b) by 0 days.

(21) Appl. No.: 09/340,027

(22) Filed: Jun. 28, 1999

Related U.S. Application Data

(63) Continuation of application No. PCT/NL98/00084, filed on Feb. 10, 1998.

(30) Foreign Application Priority Data

Feb. 10, 1997 (NL) .............................................. 1005234

(51) Int. Cl.⁷ ................................................. A61F 2/32
(52) U.S. Cl. ................................... 623/23.39; 623/23.4
(58) Field of Search ........................... 623/23.39, 23.4, 623/23.41, 22.11, 17.14, 19.12, 20.22, 21.16

(56) References Cited

U.S. PATENT DOCUMENTS

| | | | |
|---|---|---|---|
| 3,869,730 A | | 3/1975 | Skobel ............................... 3/1 |
| 4,054,955 A | | 10/1977 | Seppo ........................... 3/1.91 |
| 4,276,660 A | * | 7/1981 | Laure ....................... 623/21.16 |
| 4,714,478 A | | 12/1987 | Fischer .......................... 623/23 |
| 5,062,581 A | * | 11/1991 | Branemark ............... 623/23.41 |
| 5,147,386 A | | 9/1992 | Carignan et al. .............. 623/21 |
| 5,480,442 A | * | 1/1996 | Bertagnoli ................ 623/17.14 |
| 5,549,681 A | * | 8/1996 | Segmuller et al. .......... 623/23.4 |
| 5,580,352 A | * | 12/1996 | Sekel ....................... 623/23.27 |

FOREIGN PATENT DOCUMENTS

| | | |
|---|---|---|
| DE | 0 300 131 A2 | 1/1989 |
| DE | 37 41 488 A1 | 6/1989 |
| DE | 44 06 090 A1 | 8/1995 |
| EP | 0 145 339 A2 | 6/1985 |
| EP | 0 808 617 A2 | 11/1997 |
| FR | 0 280 424 A1 | 8/1988 |
| FR | 2 680 967 A1 | 12/1993 |
| GB | 2 223 172 A | 4/1990 |
| WO | WO 89/11837 | 12/1989 |

OTHER PUBLICATIONS

SU 749 392 (Vorosh Medicine) Jul. 23, 1980.
GB 2 250 919 A (Rodnyansky) Jun. 24, 1992.

* cited by examiner

*Primary Examiner*—Paul J. Hirsch
(74) *Attorney, Agent, or Firm*—Bacon & Thomas

(57) ABSTRACT

A hip prosthesis comprising a first fastening assembly (1, 2, 6, 12, 13) intended for being mounted in the hip bone (A) and a second fastening assembly (4, 5, 7, 14) intended for being mounted in the upper extremity of the femur (F), wherein the first (1, 2, 6, 12, 13) and the second (4, 5, 7, 14) fastening assemblies are interconnected by means of a pivotable connection (8, 108) wherein all parts (1, 2, 4, 5, 6, 7, 8) of the hip prosthesis are so small and/or slender that they can each be arranged in the intended end position thereof via a bore (9) in the femur (F), which bore (9) extends from the outside ($F_o$) of the femur (F) through the femoral neck ($F_n$) substantially in the direction of the imaginary longitudinal center line ($LF_n$) of the femoral neck ($F_n$) to the femoral head ($F_h$)

5 Claims, 20 Drawing Sheets

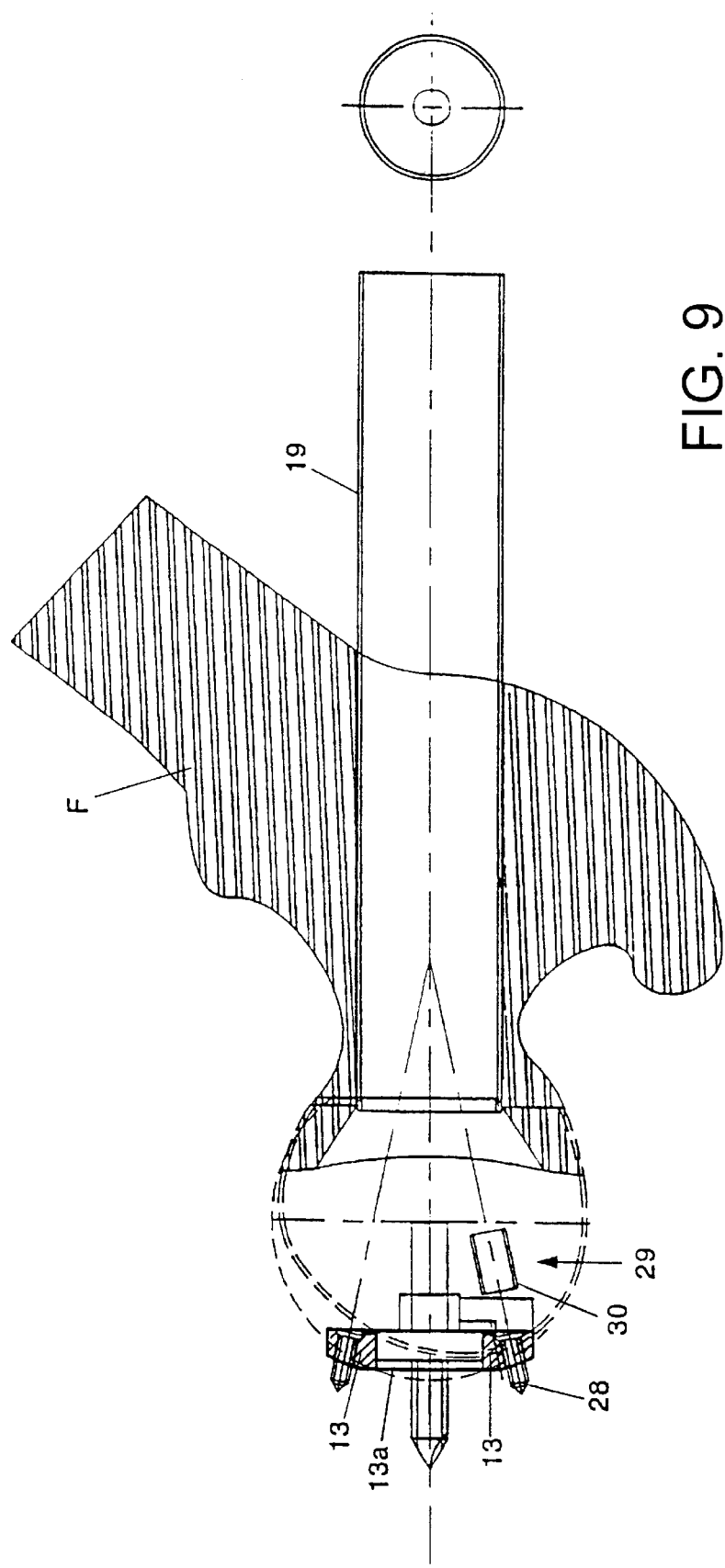

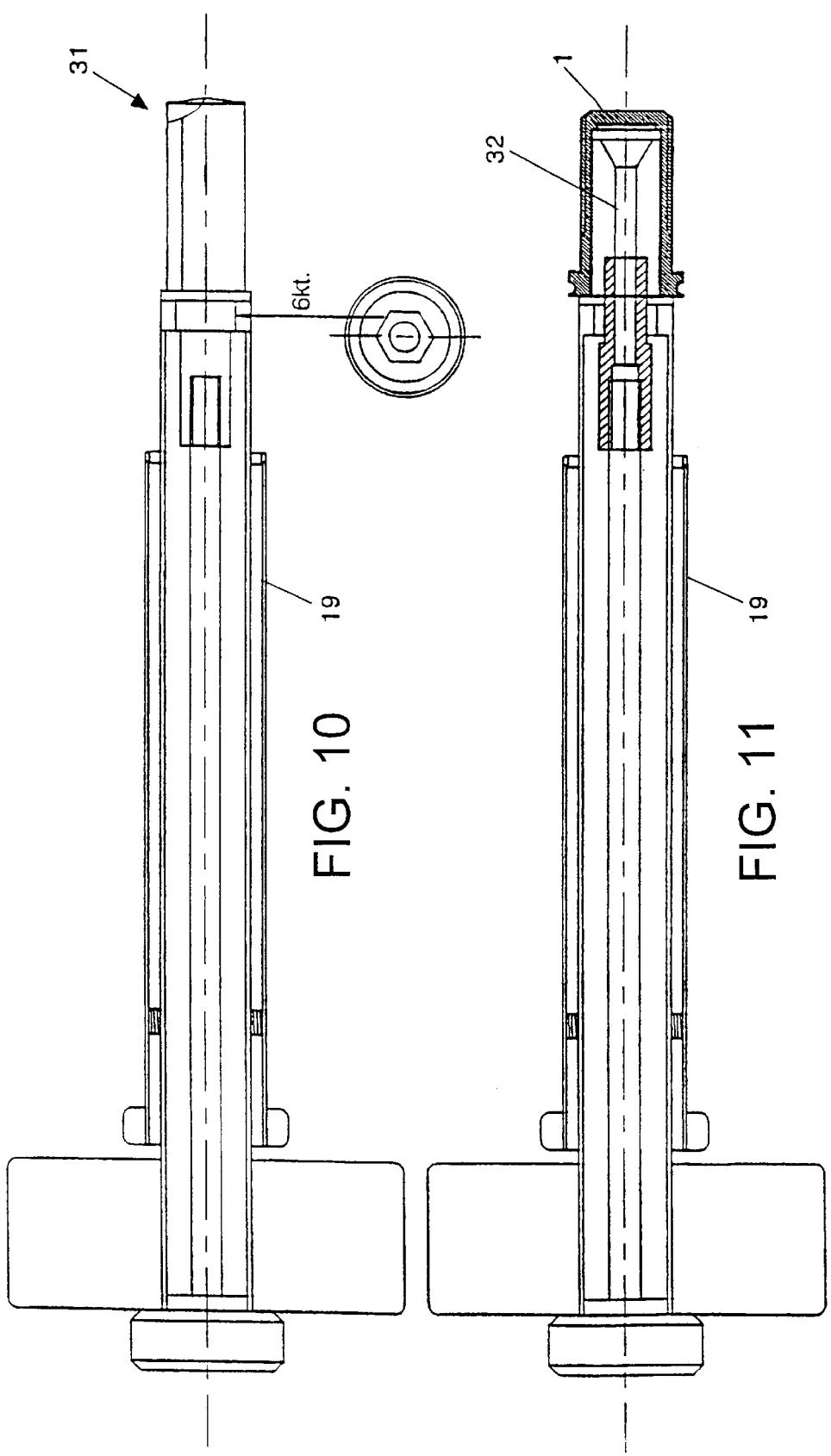

HIP PROSTHESIS AND METHOD FOR FITTING SUCH HIP PROSTHESIS

This application is a continuation of pending international application No. PCT/NL98/00084 filed Feb. 10, 1998.

The invention relates to a hip prosthesis and a method for fitting such hip prosthesis.

Examples or a known hip prosthesis and a known method for fitting such hip prosthesis are for instance described in EP-A-0 145 339. In general, such so-called total hip joint prostheses comprise two parts: a femoral head prosthesis and an acetabular prosthesis.

The known femoral head prosthesis comprises a head in the form of a hemisphere and a stein extending from the head and suitable for being secured in the medullar canal of the femur. The acetabular prosthesis comprises a hemispherical cup fixed in the acetabulum of the hip bone by means of cement, screws or the like.

A major drawback of the known hip prostheses is formed by the manner in which these hip prostheses should be fitted. This fitting involves a very difficult operation taking up a number of hours. In particular in the case of older patients, the operation is not without risks. Moreover, essential tissues, such as the joint capsula and the ligaments, are cut through, which results in a decreased stability of the joint and a long recovery period. In addition, complications may occur in the form of infections, loosening of the femoral prosthesis from the medullary canal, fractures and inflammation of the joint capsula caused by splinters or parts coming from the acetabular prosthesis. Moreover, the reaming of the medullary canal in the femur may have harmful effects, such as, for instance, micro-embolisms. The hip prostheses known from SU-A-749 392, GB-A-2 250 919 and WO-A-89 11 837 are also mounted during major operations in which the above mentioned essential tissues have to be cut through resulting in a decreased stability of the joint and a long recovery period.

The object of the invention is to provide a hip prosthesis and a method for fitting such a hip prosthesis wherein the above-described drawbacks do not occur, or at least to a smaller extent.

To this end, in accordance with the invention, the hip prosthesis comprises a first fastening assembly intended for being mounted in the hip bone and a second fastening assembly intended for being mounted in the upper extremity of the femur, wherein the first and the second fastening assembly are interconnected by means of a pivotable connection, wherein all parts of the hip prosthesis are so small and/or slender that they can each be arranged in the intended end position thereof via a bore in the femur, which bore extends from the outside of the femur through the femoral neck substantially in the direction of the imaginary longitudinal center line of the femoral neck to the femoral head.

The invention also provides a method for fitting such a hip prosthesis, wherein a small incision is made in the leg to gain access to the top part of the femur, wherein a femoral bore is subsequently made in the femur, which femoral bore extends from the outside of the femur through the femoral neck substantially in the direction of the imaginary longitudinal center line of the femoral neck to the femoral head, wherein the femoral head is subsequently removed via the femoral bore, wherein, via the femoral bore, a hip bone bore is subsequently made in the hip bone at the location of the acetabulum, wherein, via the femoral bore, the first fastening assembly is subsequently mounted in the hip bone bore and the second fastening assembly is mounted in the femoral bore, after which, finally, the incision is closed.

The hip prosthesis and the method for fitting the hip prosthesis are particularly advantageous especially because the operation is far less drastic, owing the construction of the hip prosthesis. The total replacement of the hip joint can be carried out intraluminally, i.e. via the bore in the femur. Optionally, such an operation can be carried out under local anaesthesia in an outpatients' department. At any rate, the patient's residence in the hospital can be shortened considerably, Moreover, the danger of infection is reduced considerably. A very important advantage is that the muscles, the Joint capsula and the ligaments around the joint remain untouched during the fitting of the hip prosthesis according to the invention. Further the amount of bone which has to be removed is kept minimal. A further advantage is that revision of the prosthesis or parts thereof is feasible. This was impossible during the implantation or fitting of the known prostheses, which inter alia had the result that the recovery period after the fitting of the known prosthesis was fairly long and, moreover, an extensive follow-up treatment with excercises was necessary. When fitting the hip prosthesis according to the invention utilizing the method according to the invention, damage to the tissues around the hip joint is minimized.

It is observed that U.S. Pat. No. 4,714,478 discloses a hip prosthesis which can also be fitted via a bore in the femur without damaging the joint capsula, the surrounding muscles and ligaments. However, this does not concern a so-called total hip prosthesis but only a replacement of the Femoral head. Hence, this known solution cannot be used in patients whose acetabulum is damaged. Another drawback of the known apparatus is that the femoral head prosthesis is manufactured from flexible, compressible material that can be filled with, for instance, a hardening plastic after having been brought into the desired position. During this filling, the prosthesis part positioned at the location of the original femoral head assumes the shape of a femoral head. However, a drawback is that each femoral head has a different radius and shape, so that each prosthesis should be specifically manufactured for a patient in question. This type of made-to-measure work is very costly. Moreover, it is not easy fo find materials that are on the one hand sufficiently flexible so as to be able to be folded together, and on the other hand sufficiently resistant to wear so as to be able to serve as joint surface.

The present invention is essentially based on the insight that the original ball joint comprising a cup and a ball can just as well be replaced by other pivot constructions of a much more slender design and yet having the same degrees of freedom of movement. Further elaborations of the invention are described in the subclaims and will be specified on the basis of two exemplary embodiments with reference to the accompanying drawings.

FIG. 9 shows a fitted supported ring including a drill jig for forming drill holes in the acetabulum for fixing the supporting ring;

FIG. 10 shows a tool for providing a hip bone bore;

FIG. 11 shows a tool for positioning a hip bone bush;

Figure 1:
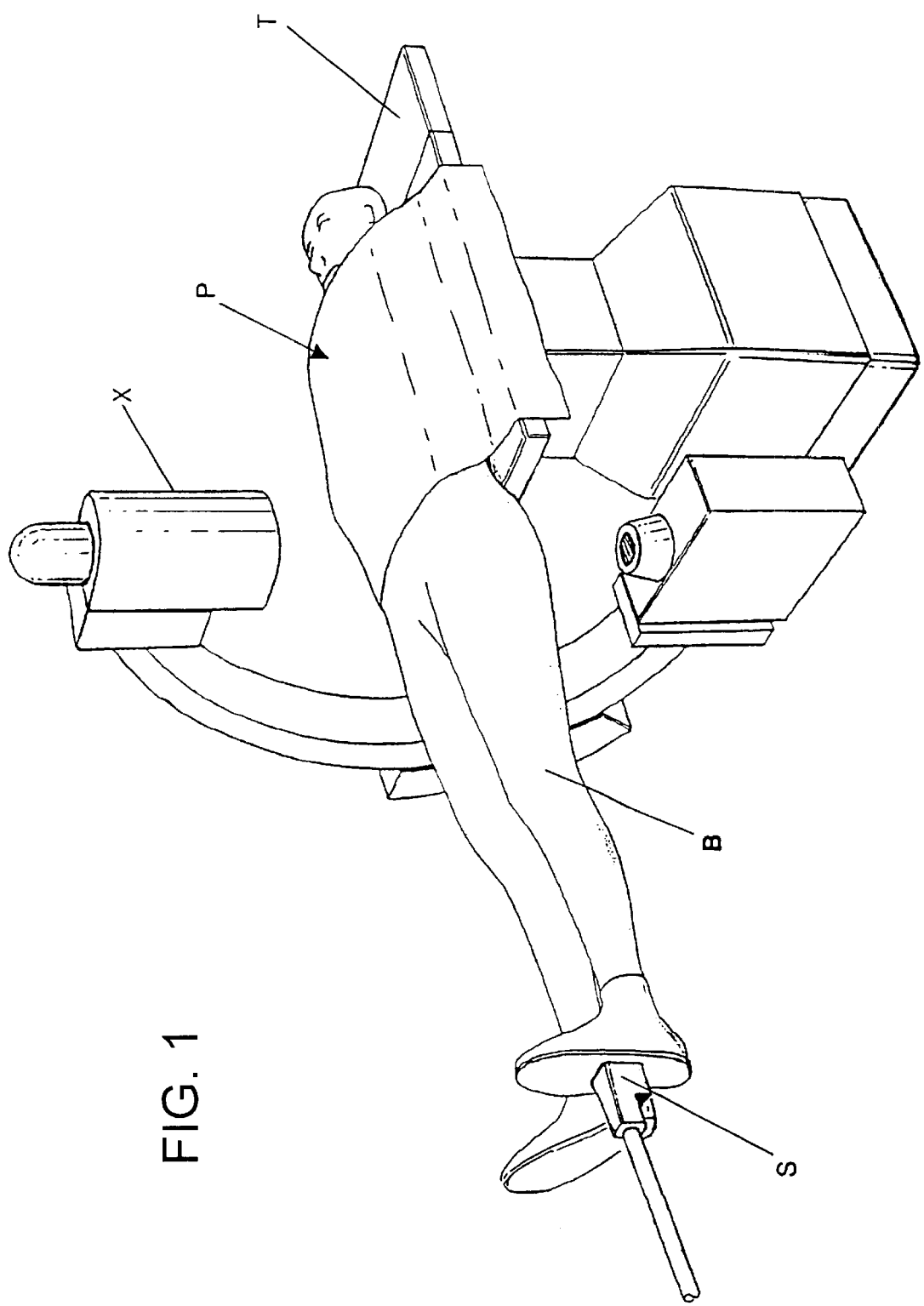
FIG. 1 shows a patient to be operated upon, on a table with X-ray equipment.

With reference to FIGS. 13–17, three exemplary embodiments of the hip prosthesis itself will first be discussed, after which the manner in which these prostheses can be fitted in the body is discussed.

As is already pointed out hereinabove, the hip prosthesis according to the invention comprises a first fastening assembly 1,2,6,12,13 intended to be mounted in the hip bone A, in particular in the ilium of the os innominatum, and a second fastening assembly 4,5,7,14 intended to be mounted in the upper extremity of the femur F. The first and second fastening assemblies are interconnected by means of a pivotable connection 8. All parts 1,2,4,5,6,7,8,10,11,13,14 are in so small and/or slender that they can each be arranged in the intended end position thereof via a bore 9 in the femur F. The bore 9 extends from the outside $F_o$ of the femur F through the femoral neck $F_n$ substantially in the direction of the imaginary longitudinal center line $LF_n$ of the femoral neck $F_n$ to the femoral head $F_h$. In general, such a bore will have a diameter in the range of 15–40 mm. In the exemplary embodiment shown, the diameter of the bore is 26 mm. The length of the bore is in the range of 40–100 mm. In the exemplary embodiment shown, this length is about 70 mm. The total length of the femoral bush 4 shown is 72 mm. It is understood that the measurements stated are only indicative and should not be construed as being limitative In any way. The first fastening assembly 1,2,6,12,13 comprises a hip bone bush 1 and a hip bone pin 2. The hip bone bush 1 is undetachably insertable into a hip bone bore 3, for instance by means of screw thread, cement, resin, porous coatings, biological ingrowth surfaces or the like or a combination of such means. The hip bone pin 2 can at least partly be accommodated in the hip bone bush 1. The second fastening assembly 4,5,7,14 comprises a femoral bush 4 and a femoral pin 5. The femoral pin 5 can at least partly be accommodated the femoral bush 4. The hip bone pin 2 and the femoral pin 5 are pivotally interconnected to form the pivotable connection 8 between the two fastening assemblies. In the present exemplary embodiment, the hip bone pin 2 and the femoral pin 5 are of cylindrical design and are rotatably accommodated in the hip bone bush 1 and the femoral bush 4 respectively. In the present exemplary embodiment, a lining 6 of a low frictional coefficient is included between the hip bone pin 2 and the hip bone bush 1. Between femoral pin 5 and the femoral bush 4, too, a lining 7 of a low frictional coefficient is included. In the exemplary embodiment shown in FIGS. 6 and 13–15, the pivotable connection 8 between the hip bone pin 2 and the femoral pin 5 is designed as a pivot 8 having a pivot pin 10 which extends by a longitudinal center line $L_1$ in a first imaginary plane $V_1$ extending perpendicularly to the center lone $L_2$ of the hip bone pin 2 and a second imaginary plane $V_2$ extending perpendicularly to the center line $L_3$ of the femoral pin 5. The pivot 10 is rotatable about the center line $L_2$ of the hip bone pin 2 in the first imaginary plane $V_1$. The pivot pin 10 is moreover rotatable about the center line $L_3$ of the femoral pin 5 in the second imaginary plane $V_2$. In this manner, a construction is obtained by means of which the femur F can adopt all positions relative to the hip A that could also be achieved with the original hip joint. The construction is highly reminiscent of a so-called cardan joint which can for instance be found in the cardan shaft of power-driven vehicles.

To prevent ingrowth of living material in the pivot 8, a flexible sleeve 11 can be provided around the pivot 8.

Figure 16:
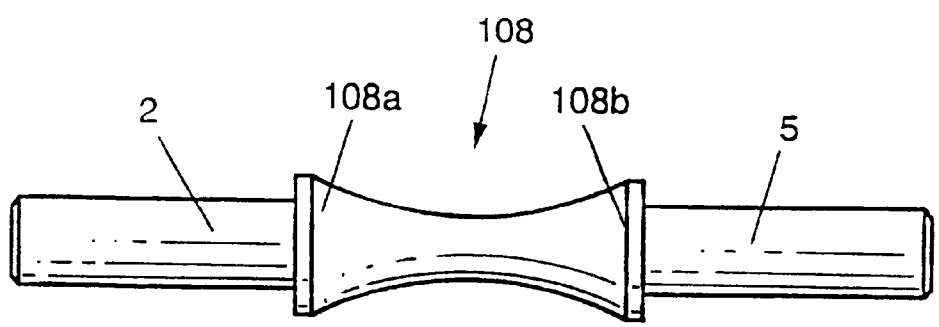
FIG. 16 shows a first alternative embodiment of a part of the prosthesis according to the invention.

FIG. 16 shows a first alternative embodiment of the pivotable connection 108 between the hip bone pin 2 and the femoral pin 5. In this alternative embodiment, the pivotable connection 108 is designed as a flexible hourglass-shaped element 108 having two end faces 108a, 108b. One end face 108a is connected to the hip bone pin 2 and the other end face 108b is connected to the femoral pin 5, so that the hip bone pin 2 and the femoral pin 5 are pivotable in all directions relative to each other. Such a pivotable connection can be found in the foot of the mast of a surfboard, wherein a flexible hourglass-shaped element forms the connection between the mast and the mast foot part that is fixed in the surfboard.

Figure 17:
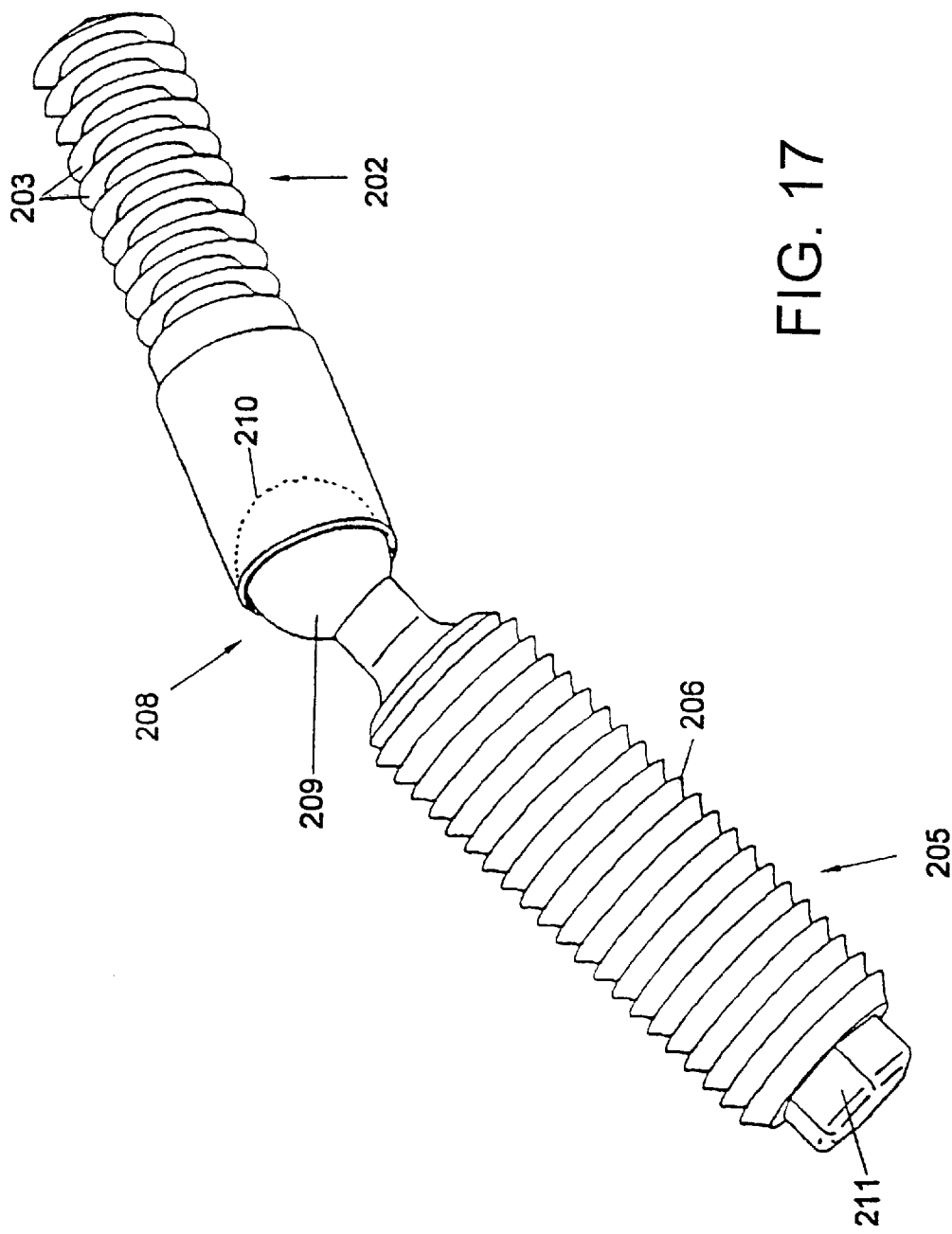
FIG. 17 shows a second alternative embodiment of the prosthesis according to the invention.

FIG. 17 shows a second alternative embodiment of the pivotal connection 208 between the first fastening assembly 202 and the second fastening assembly 205, The pivotal connection 208 is designed as a ball 209 and socket 210 assembly of which the external dimensions are smaller than the largest external dimension of the second fastening assembly 205. In the second alternative embodiment, the first fastening assembly 202 comprises a hip pin 202 having an external screw thread 203 for engaging the hip bone A. The second fastening assembly 205 comprises a femoral pin 205 having an external screw thread 206 for engaging the femoral bone F. Because of the ball and socket pivot, the first and second fastening assemblies can rotate and swivel in all directions relative to each other. In view thereof, the first and second fastening assemblies 202, 205 can be designed as simple pins which are directly mounted in the hip bone A and the femur F. However, it is also possible that the first and second fastening assemblies would comprise a hip bone bush and a hip bone pin, respectively a femoral bush and a femoral pin, wherein the respective pins are rotatably mounted in the respective bushes and the bushes are mounted in the bones.

Figure 18:
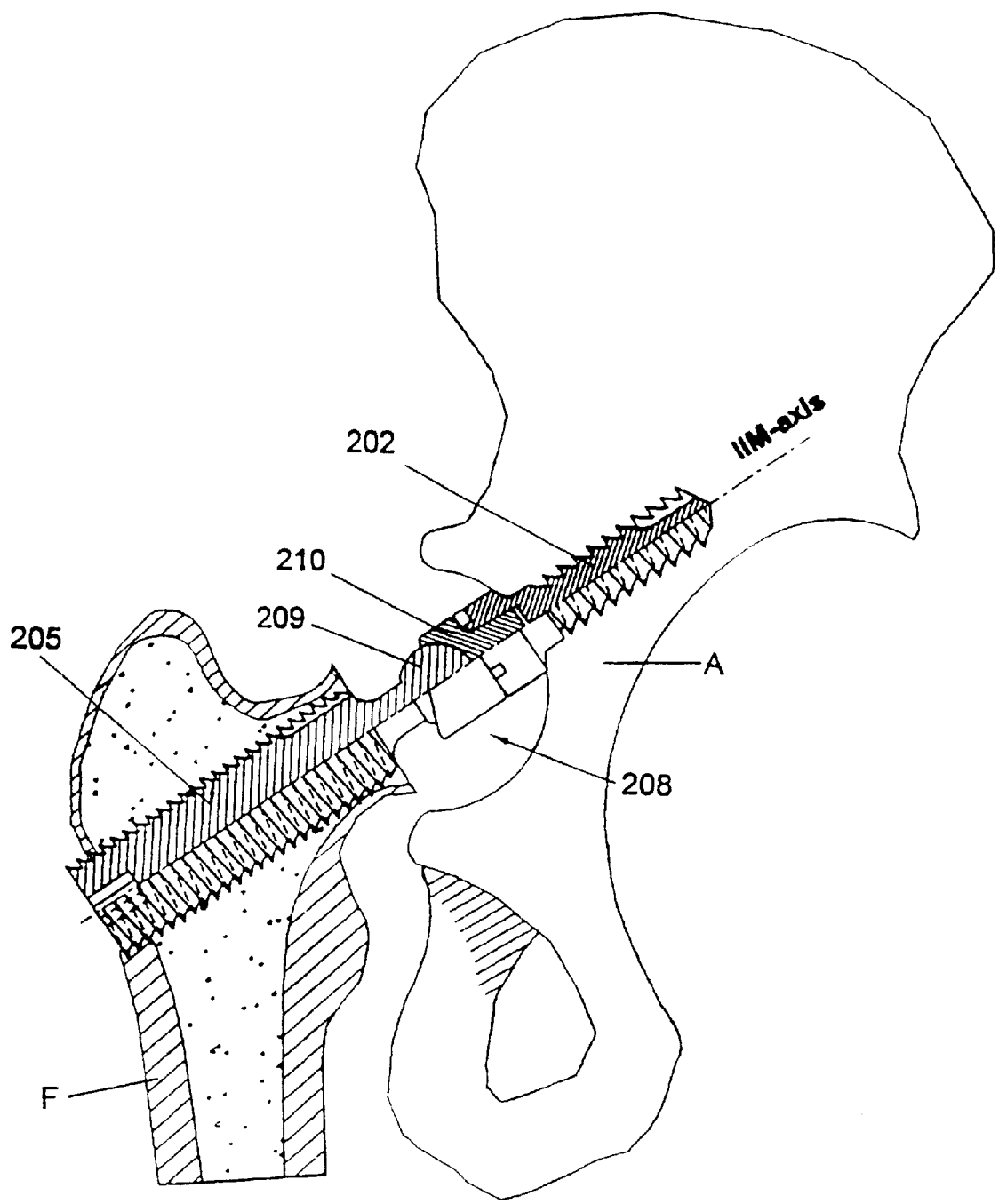
FIG. 18 shows the second alternative embodiment in a mounted condition.

FIG. 18 shows the second alternative embodiment of FIG. 17 in a mounted condition.

Figure 19:
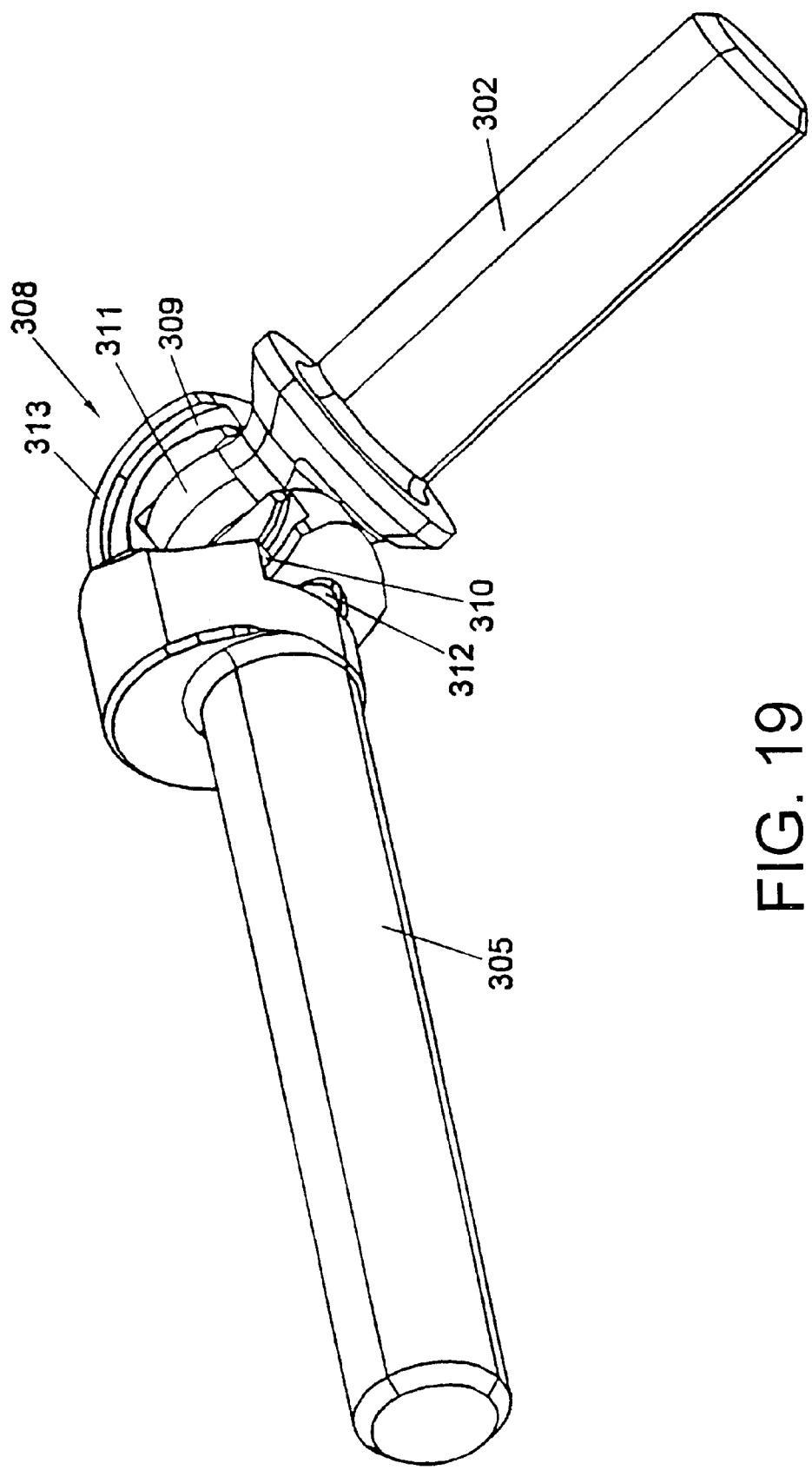
FIG. 19 shows a third alternative embodiment of the prosthesis according to the invention.

FIG. 19 shows a third alternative embodiment of the prosthesis according to the invention. The third embodiment comprises a hip pin 302 which forms part of the first fastening assembly which also comprises a hip bone bush, which has to be mounted in the hip bone A and which is not shown in FIG. 19. The second fastening assembly comprises a femoral pin 305 and a femoral bush which is not shown in FIG. 19. The femoral bush has to be fixed in the femur F. The pivotal connection 308 between the hip bone pin 302 and the femoral pin 305 comprises a first pivot which is formed by a pivot shaft 312 and a pivot shaft bore which is formed in an end part 311 of the hip bone pin 302. A pivot possibility along a second axis has been provided by an intermediate piece 313 which comprises a circular guideway 309. The femoral pin is provided with a circular notch which slideably engages the circular guide in the intermediate piece 313.

Figure 20:
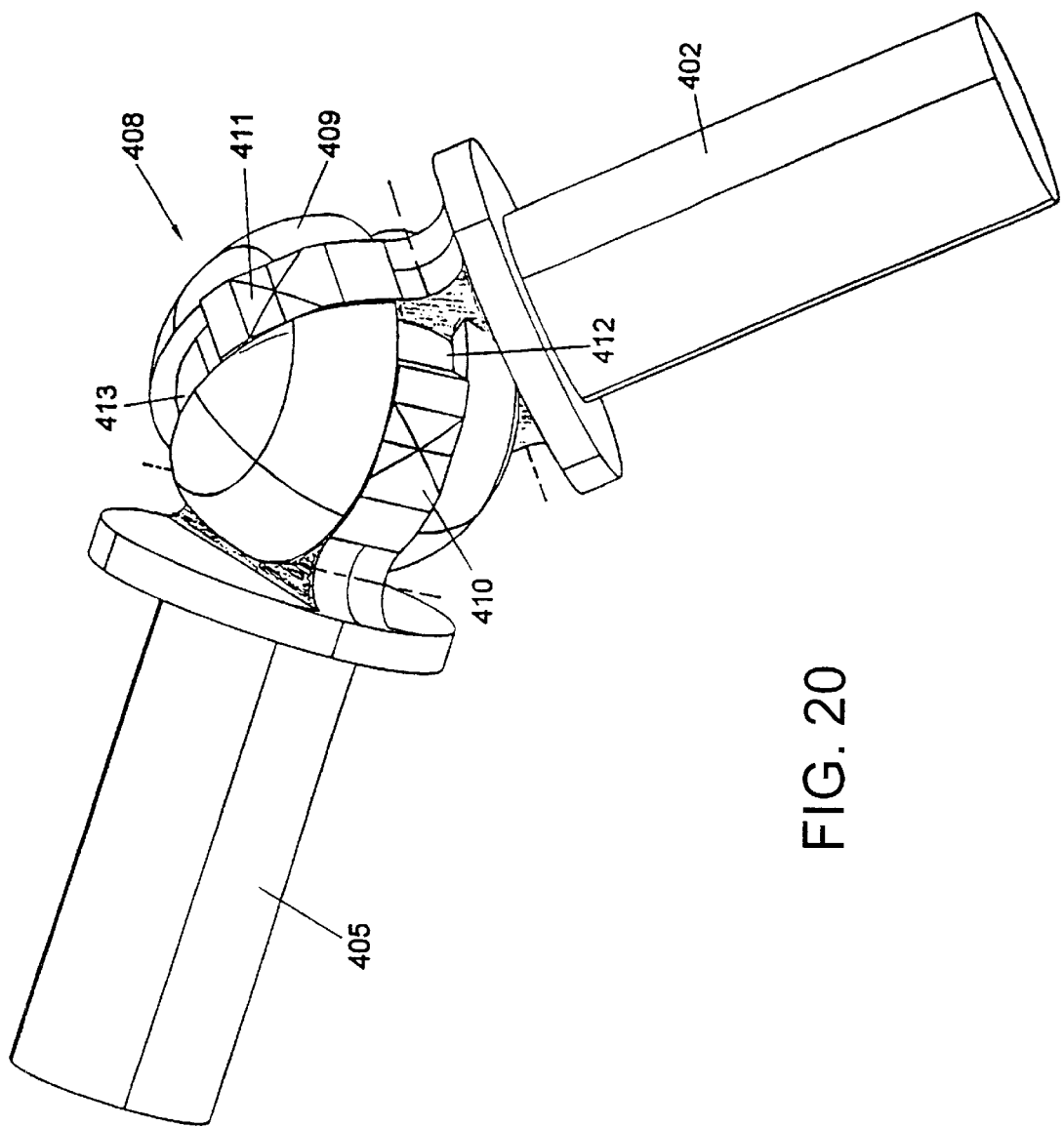
FIG. 20 shows a fourth alternative embodiment of the prosthesis according to the invention.

A fourth embodiment of the invention is shown in FIG. 20. The first fastening assembly comprises a hip bone pin 402. The second fastening assembly comprises a femoral bone pin 405. The pivotal connnection 408 of the fourth embodiment comprises an intermediate part 409 which is a ball provided with two circular guideways 412 and 413. In the first guideway 412 a fork-like end part 410 of the femoral pin 405 engages. In the second guideway 413 a similar fork-like endpart 411 of the hip bone pin engages. Because the surfaces of the fork-like end parts 410, 411 which are directed to the intermediate ball shaped part 409 have a circular configuration, a pivotable motion of the hip bone pin 402 and the femoral pin 405 relative to the intermediate ball shaped part 409 is possible.

Figure 22:
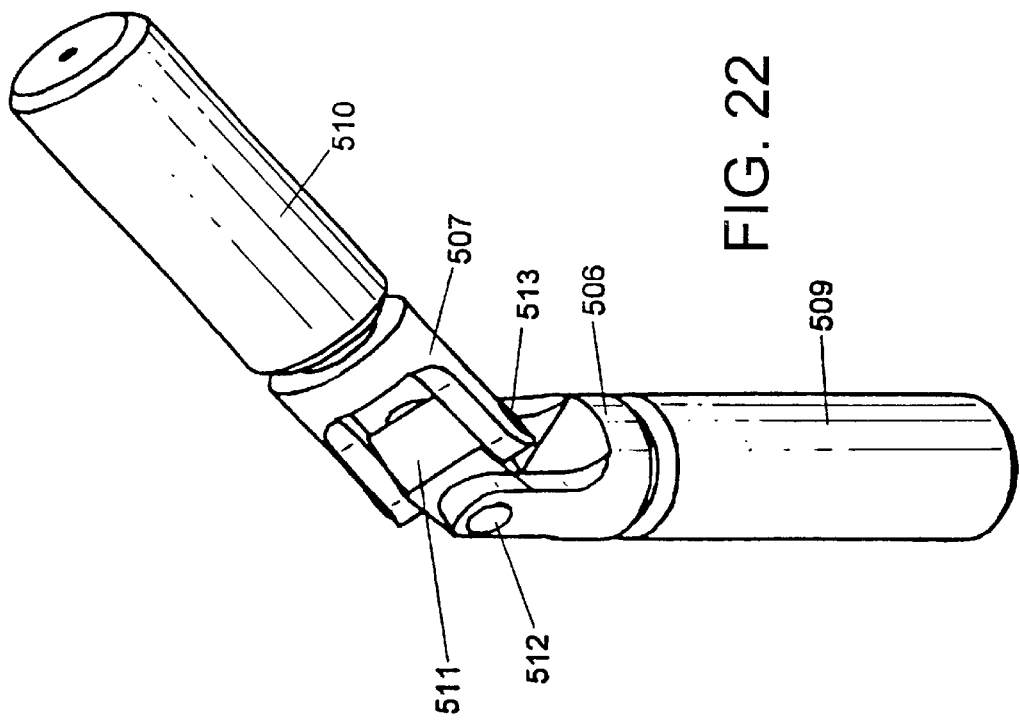
FIGS. 21–23 show a fifth embodiment of the prosthesis according to the invention.
Figure 21:
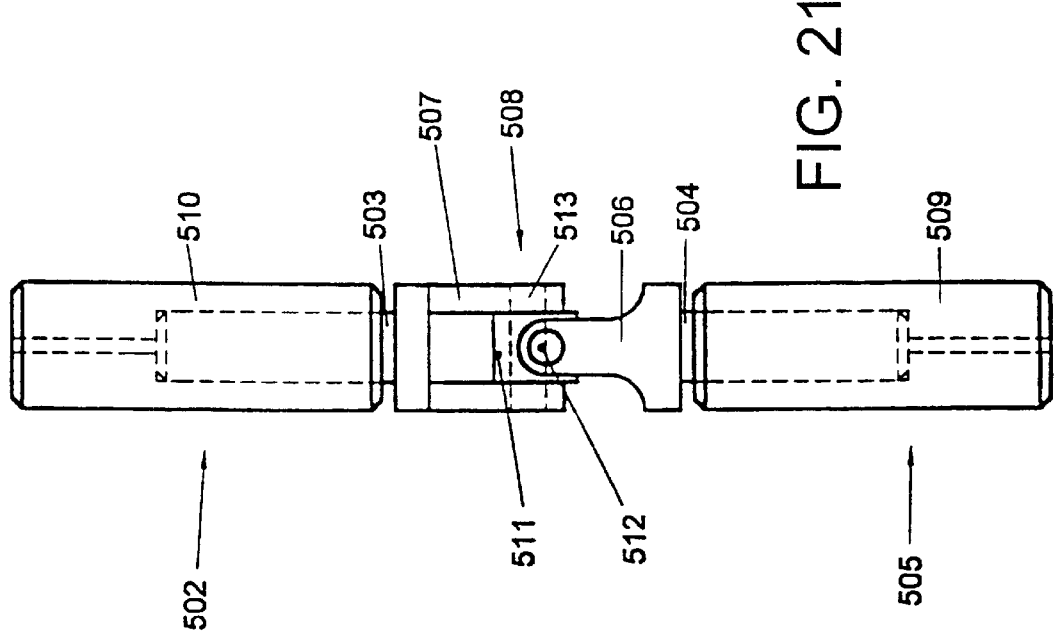
Figure 23:
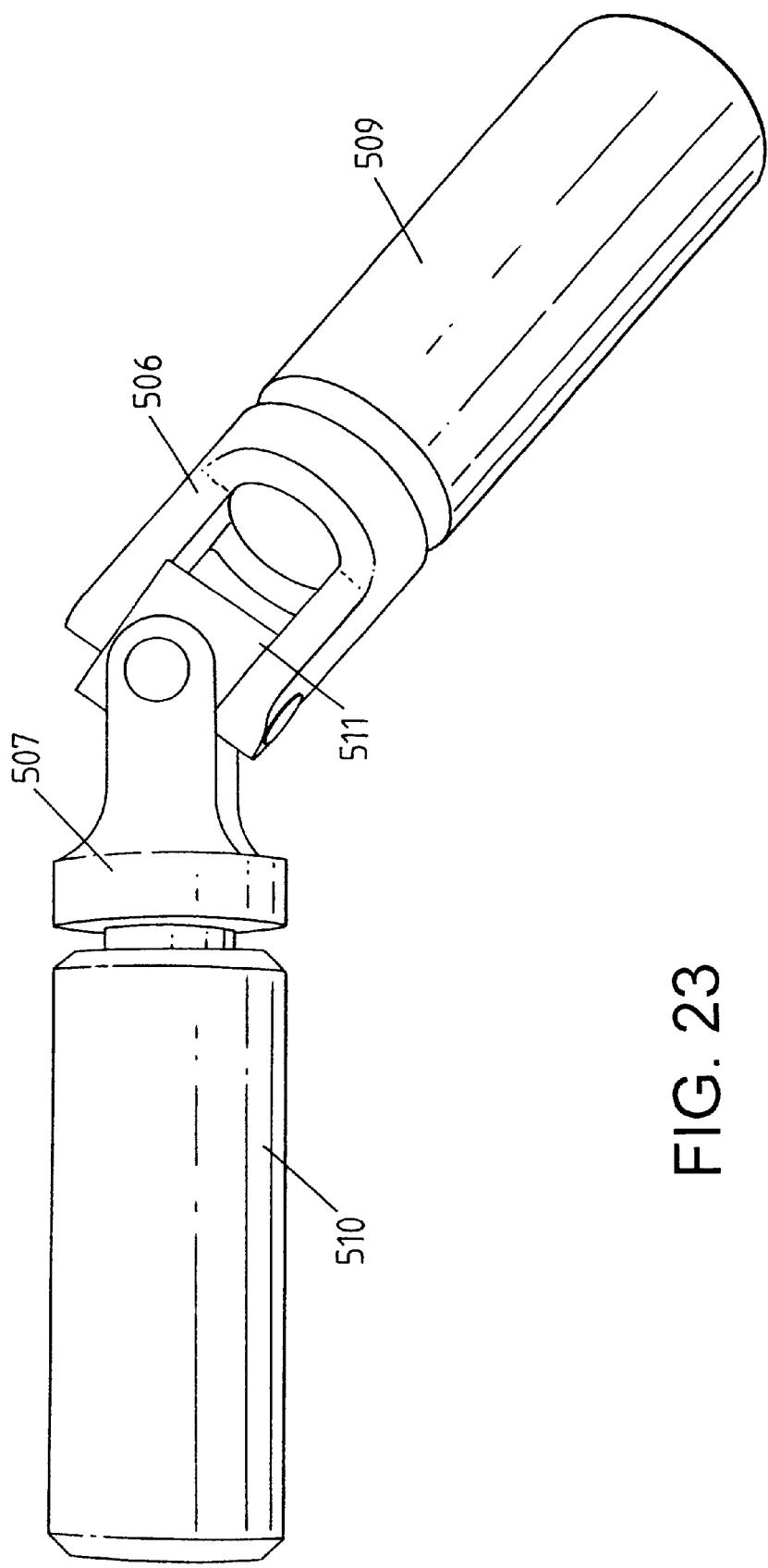

FIGS. 21–23 show a fifth embodiment of a prosthesis according to the invention. The pivotal connection between the first fastening assembly 502 and the second fastening assembly 505 is formed by a cardan coupling. The first fastening assembly 502 comprises a hip bone bush 510 and a hip bone pin 503. The hip bone pin 503 is provided with a fork-like member 507. The second fastening assembly comprises a femoral bush 509 and a femoral pin 504. The femoral pin is provided with a fork-like member 506. The fork-like members 506, 507 are connected to each other via an intermediate piece 511 with two shafts 512, 513. The shafts 512, 513 are orientated perpendicularly relative to each other. This embodiment has a relative simple construction which is solid and has a great freedom of movement.

As mentioned hereinabove, all parts of the hip prosthesis should be so small and/or slender that they can be arranged in the intended end position thereof via a bore 9 in the femur F, which bore 9 extends from the outside $F_o$ of the femur F through the femoral neck $F_n$ substantially in the direction of the imaginary longitudinal center line $F_n$ of the femoral neck $F_n$ to the femoral head $F_h$. Perhaps unnecessarily, it is observed that the second fastening assembly, intended for being mounted in the upper extremity of the femur, comprises a femoral bond bush 4 which, in the mounted condition of the prosthesis, forms the connection between the femoral bone F and other parts of the prosthesis. This femoral bush 4 is in engagement with the bore 9 in the femur F.

In this connection, 'femoral bush' should be understood to mean any body having a sidewall that is undetachably connectable to a bore in the femur, which sidewall bounds a certain section and has a particular length. In general, the bush will have a circular outside contour whose diameter is in the range of about 15–40 mm. The length of the femoral bush will be in the range of about 40–100 mm. It is observed that the outside contour of the femoral bush 4 is not limited to a circular contour. Polygonal or elliptic sections or other shapes are within the bounds of possibility.

Presently, with reference to FIGS. 1–6 and 7–15, two variants of the method according to the invention will be described.

FIG. 1 shows a patient P on a table T provided with an x-ray/x-ray detection apparatus X. By means of this X-ray/ X-ray detection apparatus, the shape and the position of the femur F can be accurately observed. With a support S, the leg B of the patient P is held in a fixed position, at least during the provision of the bore 9 in the femur F. It is that other means for visualization such as arthroscopic control are possible.

Figure 2:
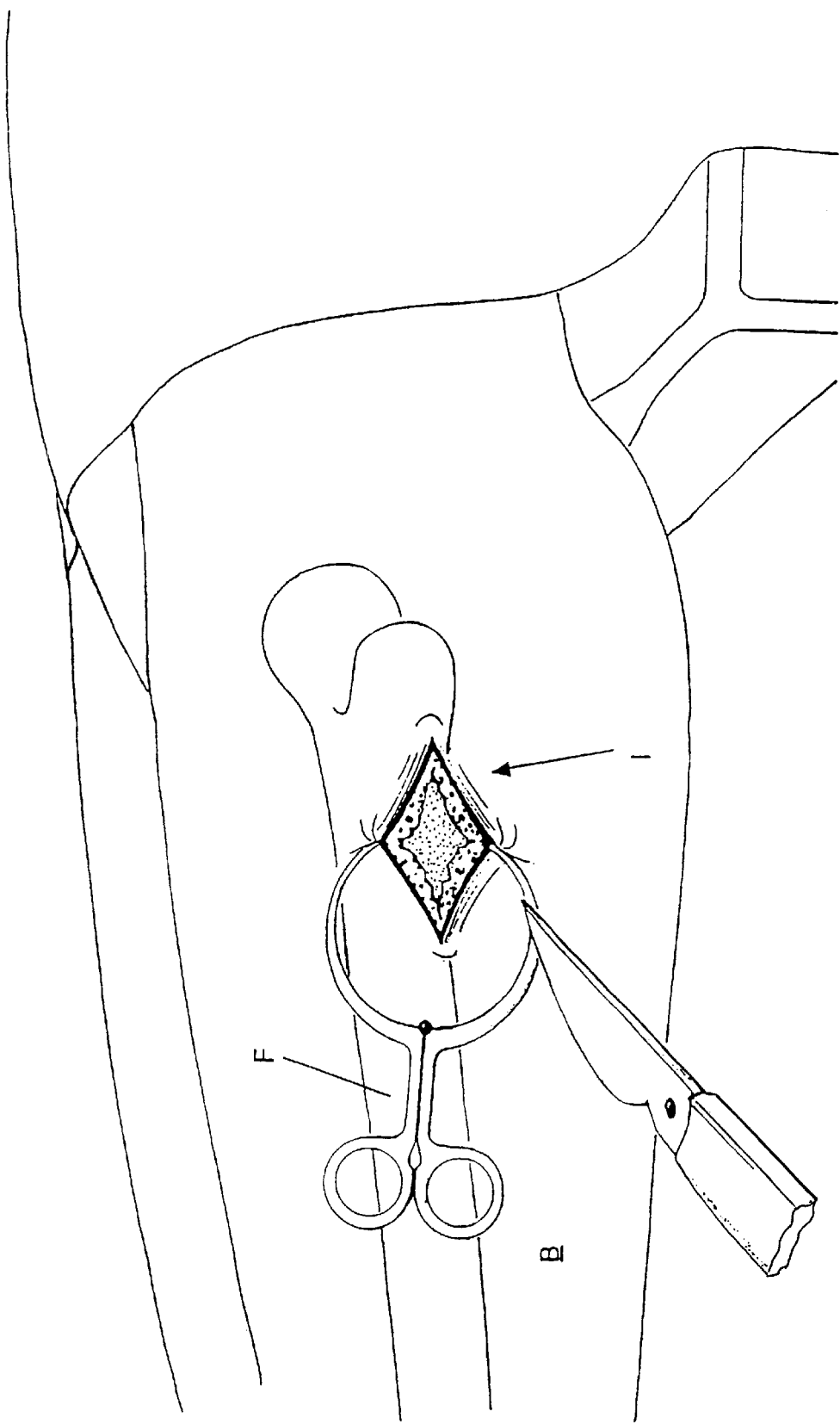
FIG. 2 shows the left leg of a patient wherein an incision has been made.
Figure 3:
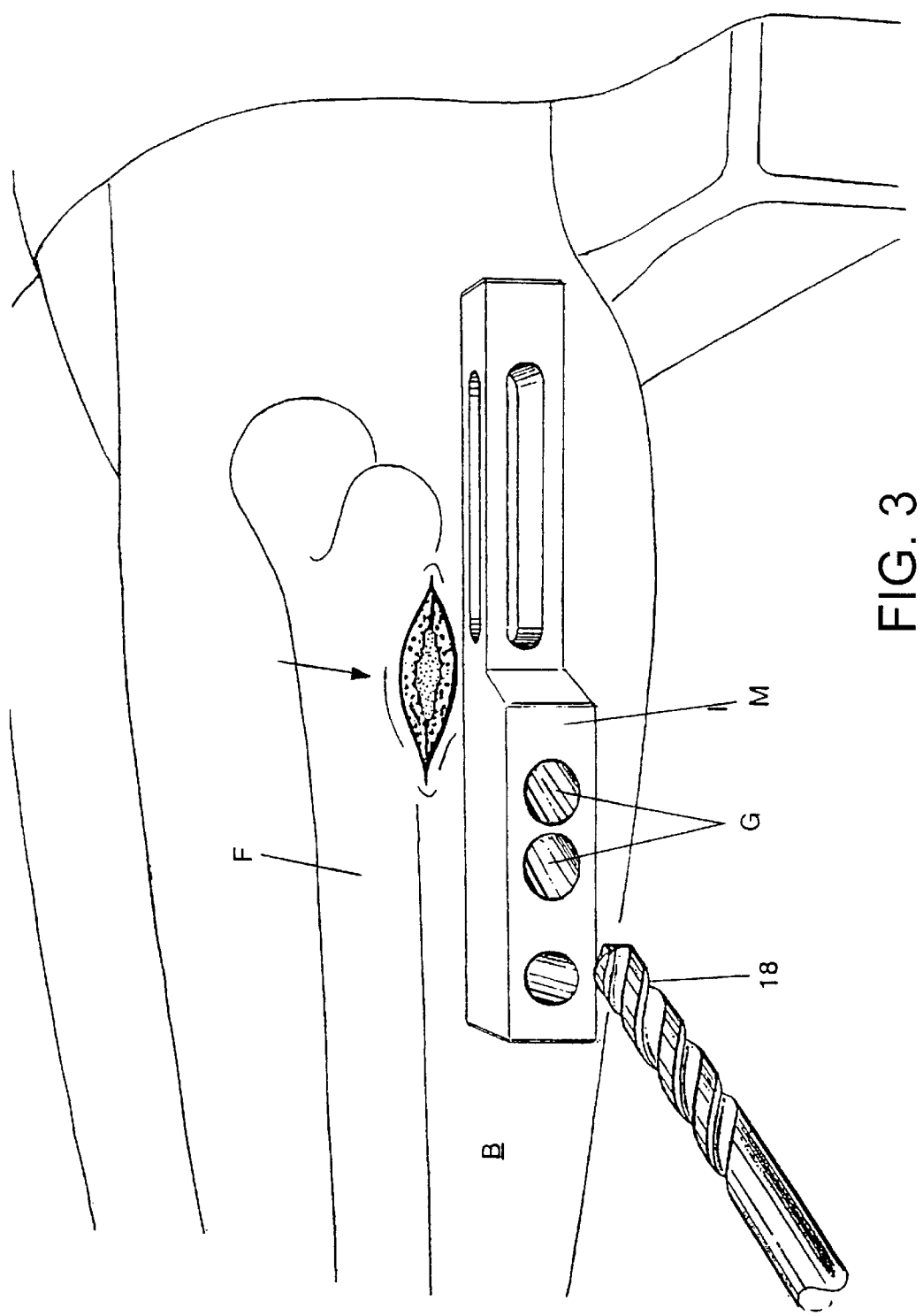
FIG. 3 shows a drill jig by means of which a desired bore can be made in the femur.

Next, as indicated in FIG. 2, a small incision I is made in the leg B, by means of which the orthopedist can gain access to the femur F. In this context, 'small' should be understood to mean: small relative to the incisions that are necessary for the conventional hip-replacing operations. One may think of an incision of a length of about 20–150 mm. Then, as shown in FIG. 3, by means of the X-ray/X-ray detection apparatus, a drill jig M can be positioned or the leg B and for instance secured by belts. The jig M is provided with holes G through which the drill 18 can be slidably and fittingly received. The jig M gives the orthopedic surgeon more control during the provision of the bore 9 in the femur F, so that during drilling, he is not exclusively dependent on the X-ray image but may also, during the drilling operation, rely on the correct positioning of the jig which has been accurately positioned prior to drilling. Subsequently, a thin-walled guide tube 19 can be accommodated in the thus obtained bore 9, through which guide tube the different tools can be brought to the interior of the hip joint, and through which the different parts of the hip prosthesis can also be fitted in the ultimately intended position.

Figure 4:
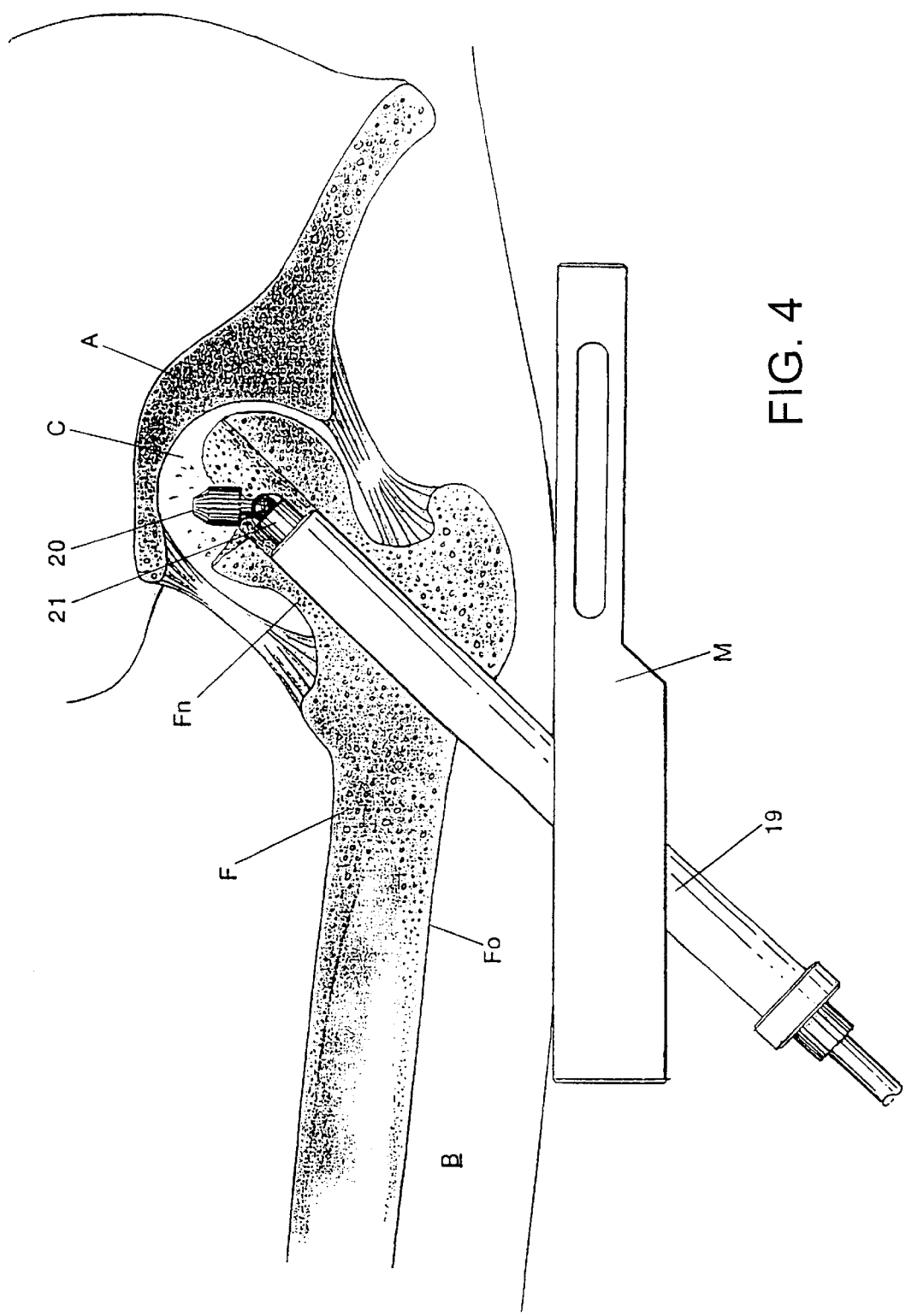
FIG. 4 is a sectional view through the hip joint while the hip head is being removed.

FIG. 4 shows the treatment following the provision of the bore 9 and consisting in removing the femoral head $F_h$ by means of a tool 20 which, in the exemplary embodiment shown, comprises a type of cylinder head cutter 20 that is pivotable relative to a drive rod 21. The drive rod 21 rotates the cylinder head cutter 20 so that the femoral head $F_n$ can thus be gradually removed. It is understood that the bone splinters released through the cutting operation should be removed from the joint cavity C after or during the cutting operation, This can for instance be effected by means of a combined rinsing and exhausting operation.

Figure 5:
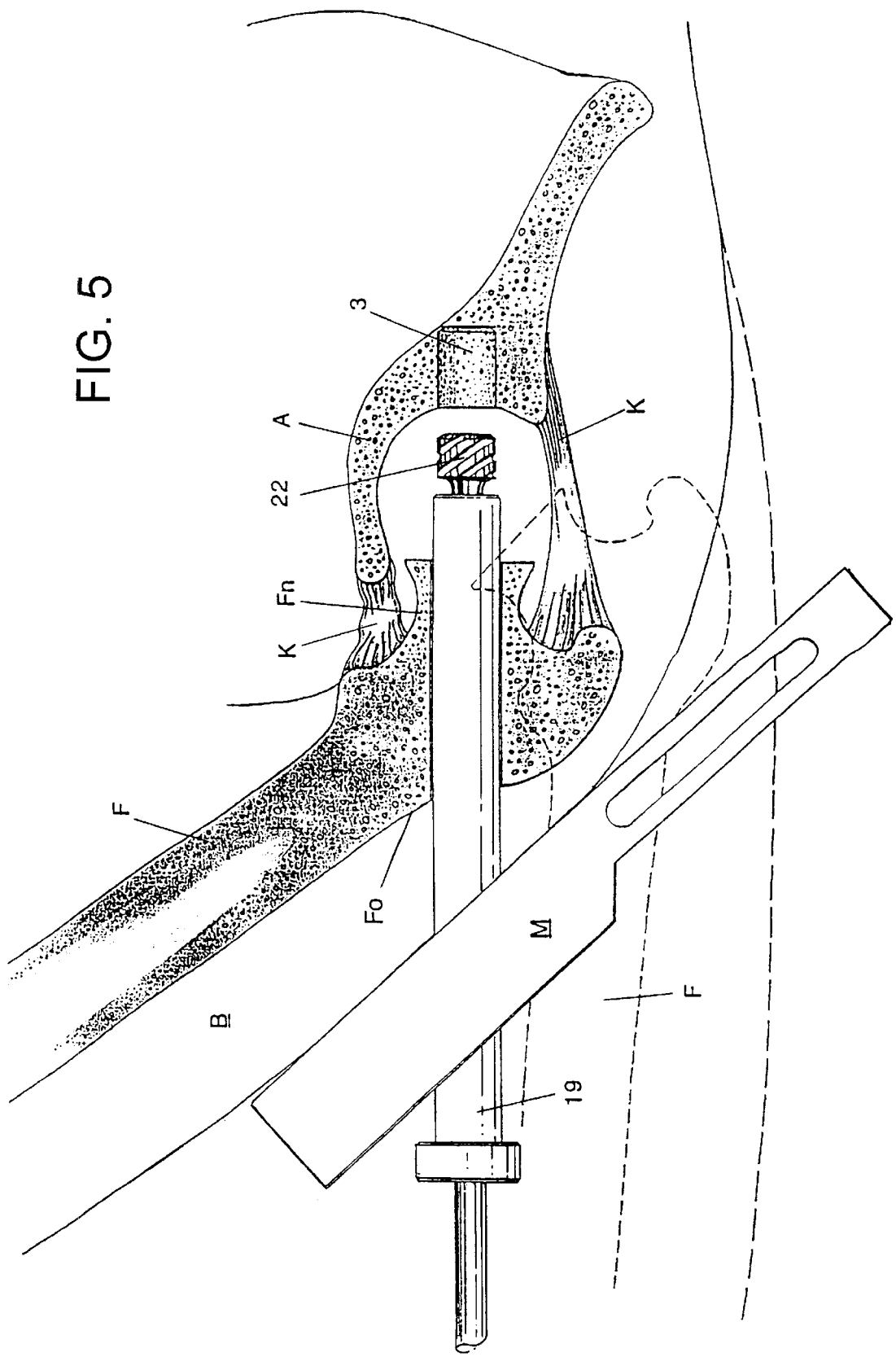
FIG. 5 is a similar sectional view wherein a bore is made in the hip bone.
Figure 6:
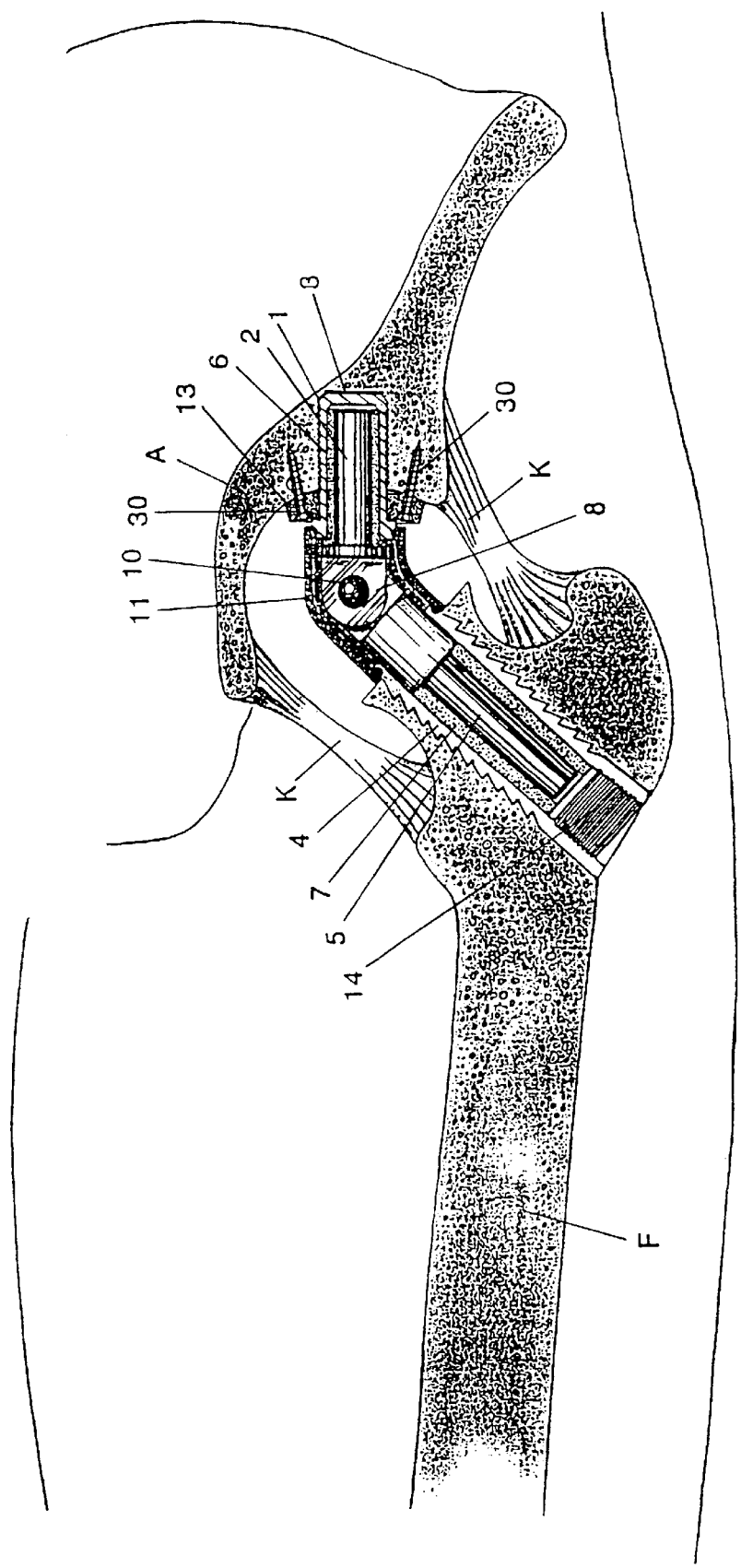
FIG. 6 shows a section of the hip joint with the hip prosthesis having been fitted.

Then, the leg B is taken from the fixed position of FIG. 1 and tilted relative to the hip bone A. This tilted position is shown in FIG. 5, wherein the original position of the femur F and the leg B are shown in dotted lines. In this tilted position, a bore 3 can then be made in the hip bone A by means of a drill or, as shown in FIG. 5, a cylinder head cutter 22. After this bore 3 has been made, the different parts of the hip prosthesis can then be brought into position. This comprises, inter alia, inserting the hip bone bush 1 into the hip bone bore 3. Then, the lining 6 together with the hip bone pin 2, the pivot 8, the femoral pin 5 and the lining 7 associated therewith can be fitted in one operation, after which the femoral bush 4 is screwed into the femur while centering the femoral pin 5. Finally, the locking plug 14 can be screwed into the femoral bush 4 in order to render the distance between the hip bone A and the femur F equal to the distance which existed in the original, natural joint, as a result of which the tension on the surrounding muscles and ligaments K is equal again to the original tension. After this, the incision I can be closed and the operation is completed.

Figure 7:
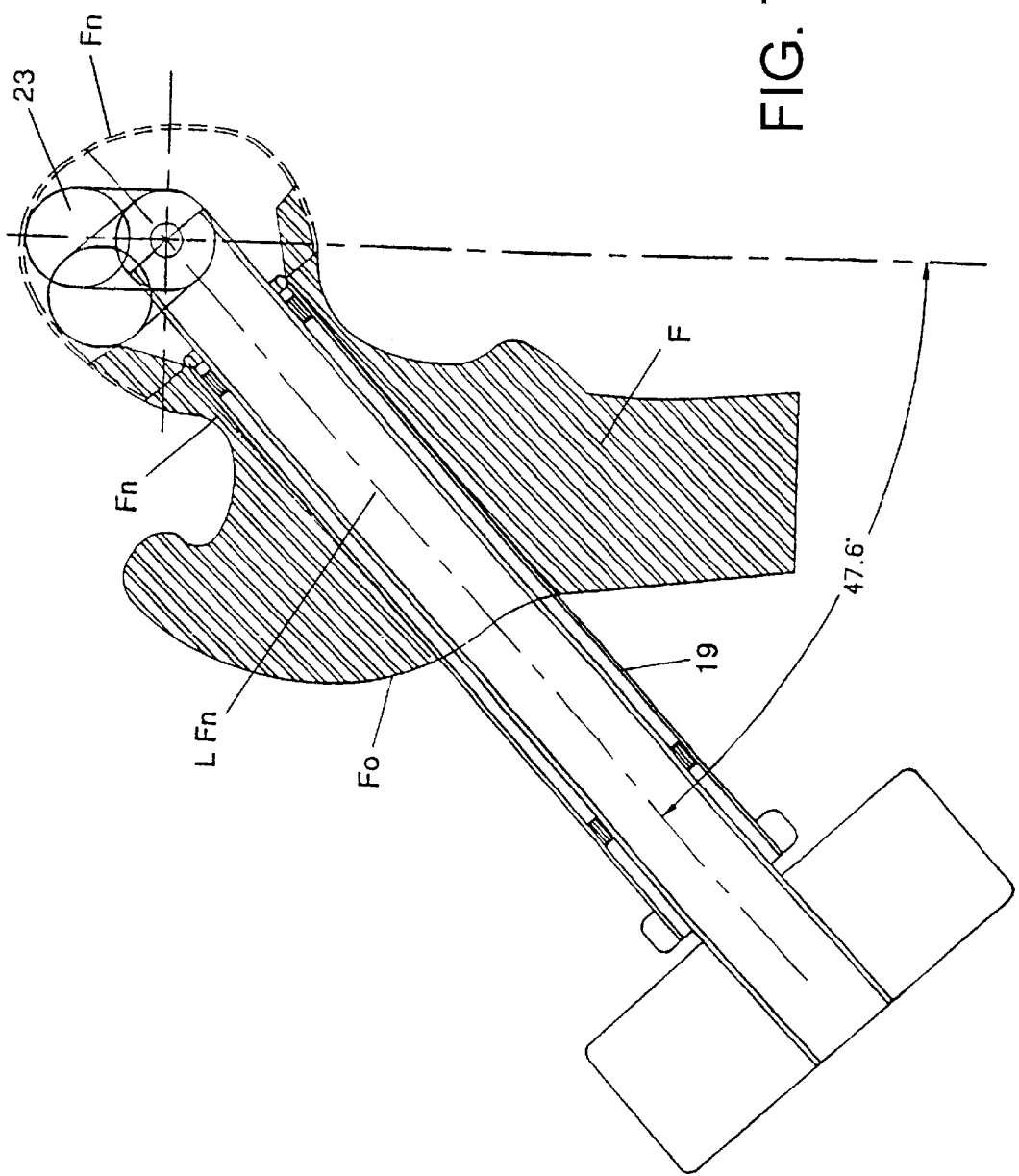
FIG. 7 shows a tool by means of which the hip head can be removed.
Figure 8:
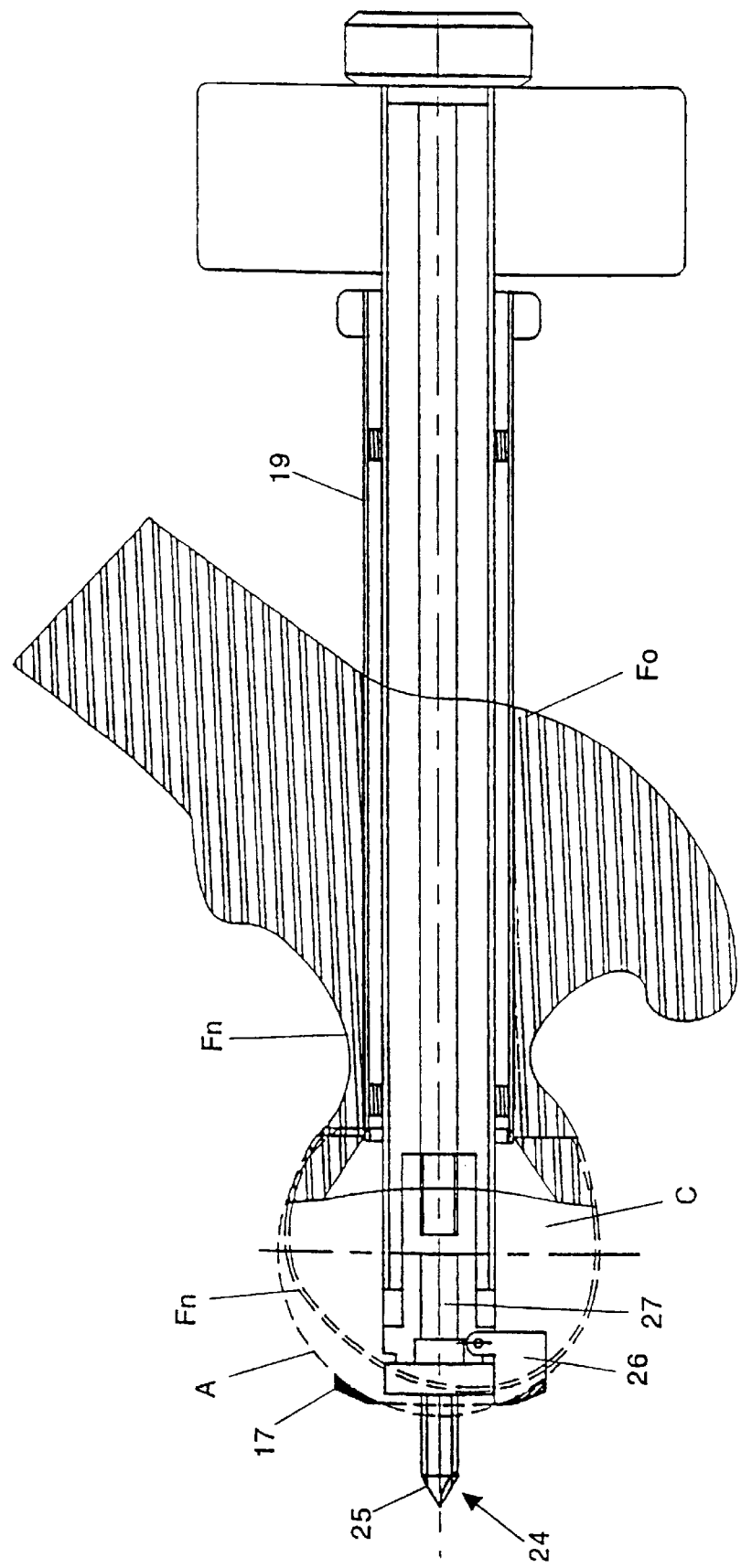
FIG. 8 shows a tool by means of which a face can be formed in the acetabulum for accommodating a supporting ring.

FIGS. 7–15 show a similar operation with slightly different tools in some more detail. In FIG. 7, the bore 9 in the femur F has already been made and also included the bore 9 is a guide tube 19. Through this guide tube 19, different tools can be moved inside. With the tool 23 shown in FIG. 7, representing a type of pliers, the cortex of the femoral head $F_h$ can be removed without releasing too small bone splinters that are hard to remove. Subsequently, a next tool 24 is introduced into the guide tube 19, which tool 24 comprises a centering drill pin 25 and an extensible face cutter 26 which is pivotally connected to the rod 27. In the collapsed position of the face cutter 26, the tool 24 can be moved through the guide tube 19. When the tool 24 is located in the joint cavity C, the face cutter 26 can be extended and by means of the face cutter 26, a supporting ring face 17 can be provided in the acetabulum A. After the provision of this supporting ring face 17, the face cutter 26 can be collapsed again, after which the tool 24 can be withdrawn from the guide tube 19. Subsequently, the supporting ring 13 as shown in FIG. 9 can be fitted. The supporting ring 13 consists of a number of segments which can be fixed separately. Each segment can for instance be secured by means of a screw 28 which can be arranged into the desired position via an auxiliary tool 29 comprising a guide bush 30. Preferably, the segments of the supporting ring 13 are designed to interlock, while in the interlocking condition of the segments, a stiff ring 13 is obtained. After the supporting ring 13 has been fitted, the bore 3 can be made in the hip bone by means of the drill 31, shown in FIG. 10, after which the hip bone bush 1 can be engaged by the tool 32 shown in FIG. 11 through sucking action and inserted into the bore 3.

Figure 12:
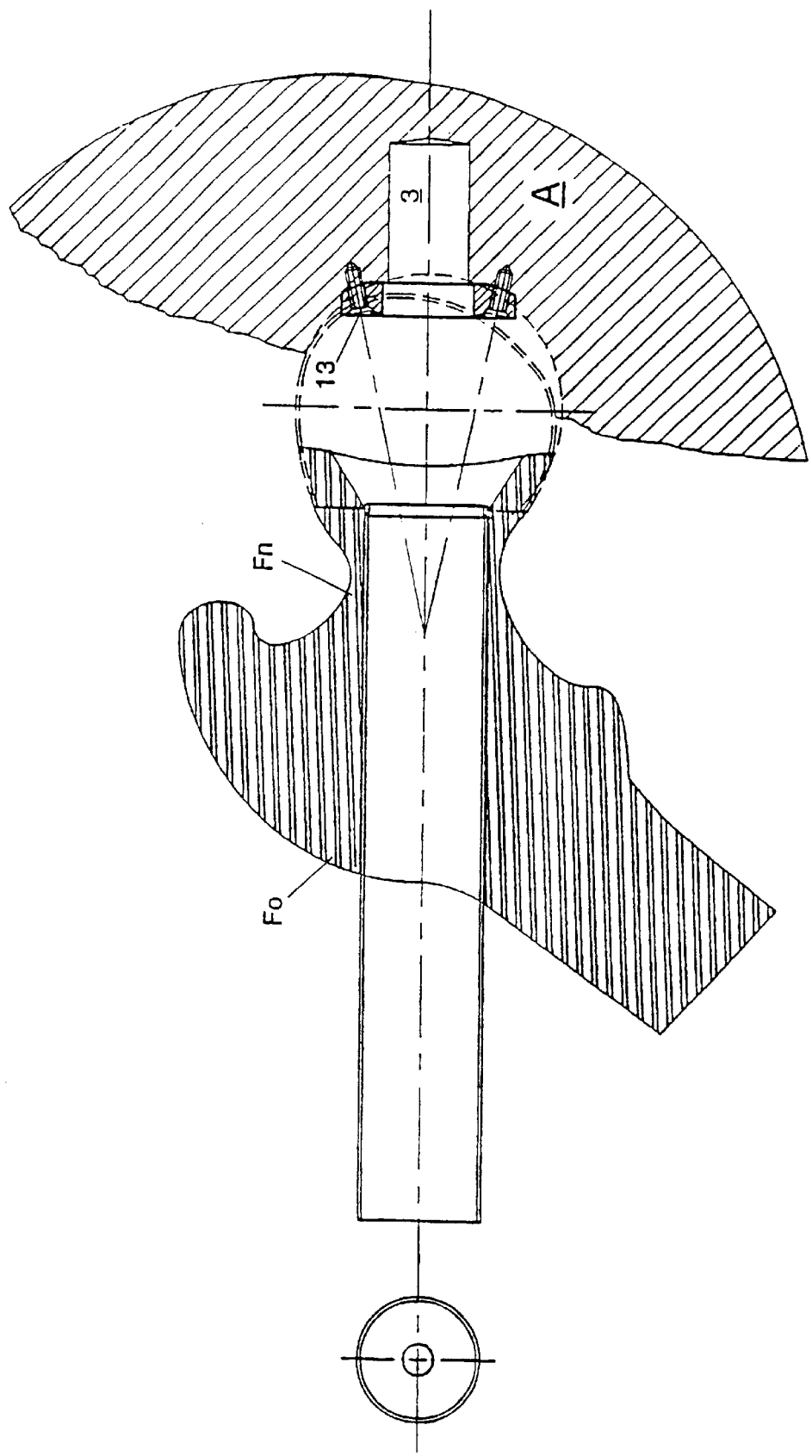
FIG. 12 is a similar view as presented in FIG. 9, with the hip bone bore having been provided.

FIG. 12 shows the hip bone A in section, wherein the bore 3 has been made and the supporting ring 13 has also been positioned.

Figure 13:
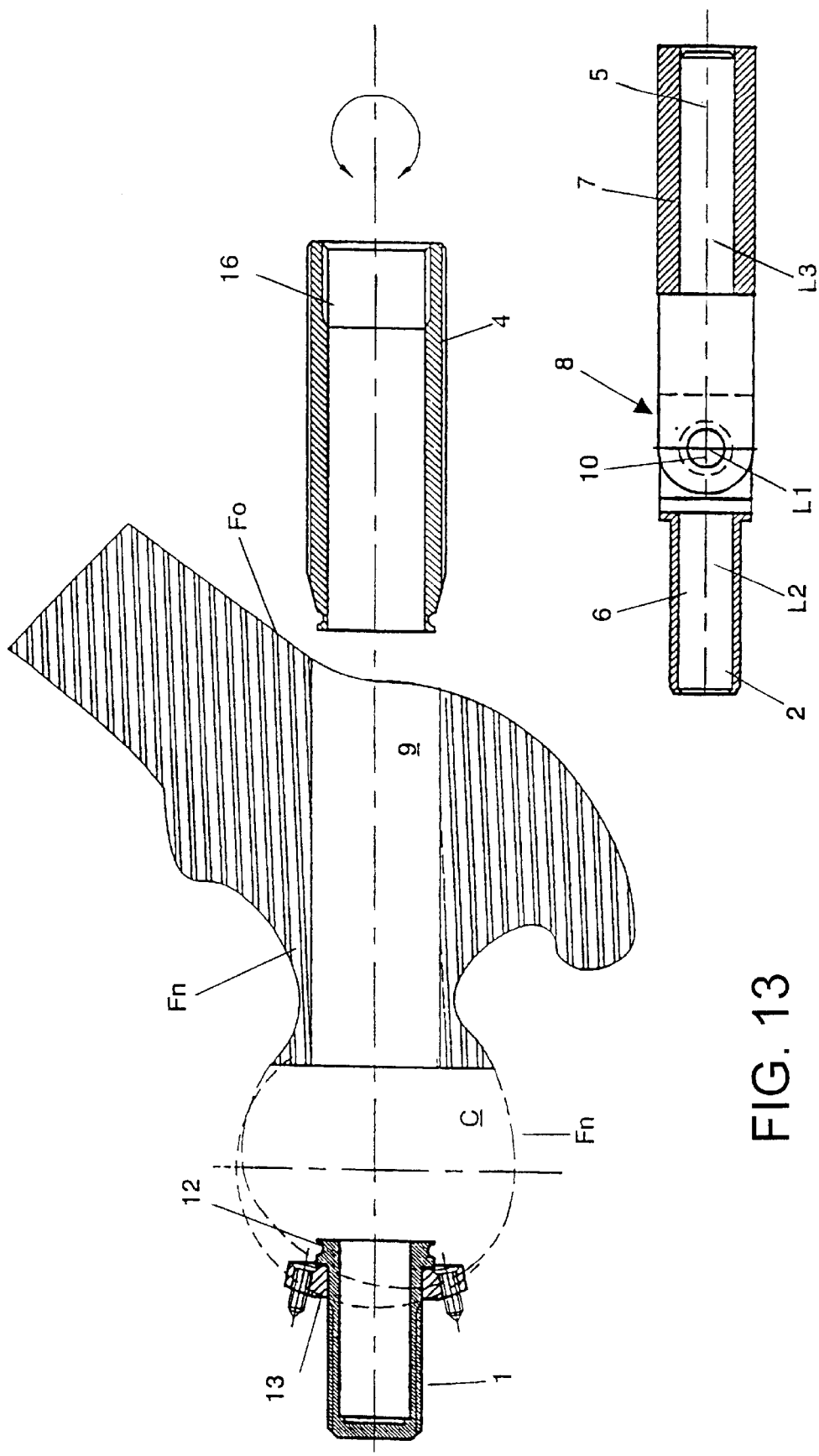
FIG. 13 shows the different components of the hip prosthesis separately.
Figure 15:
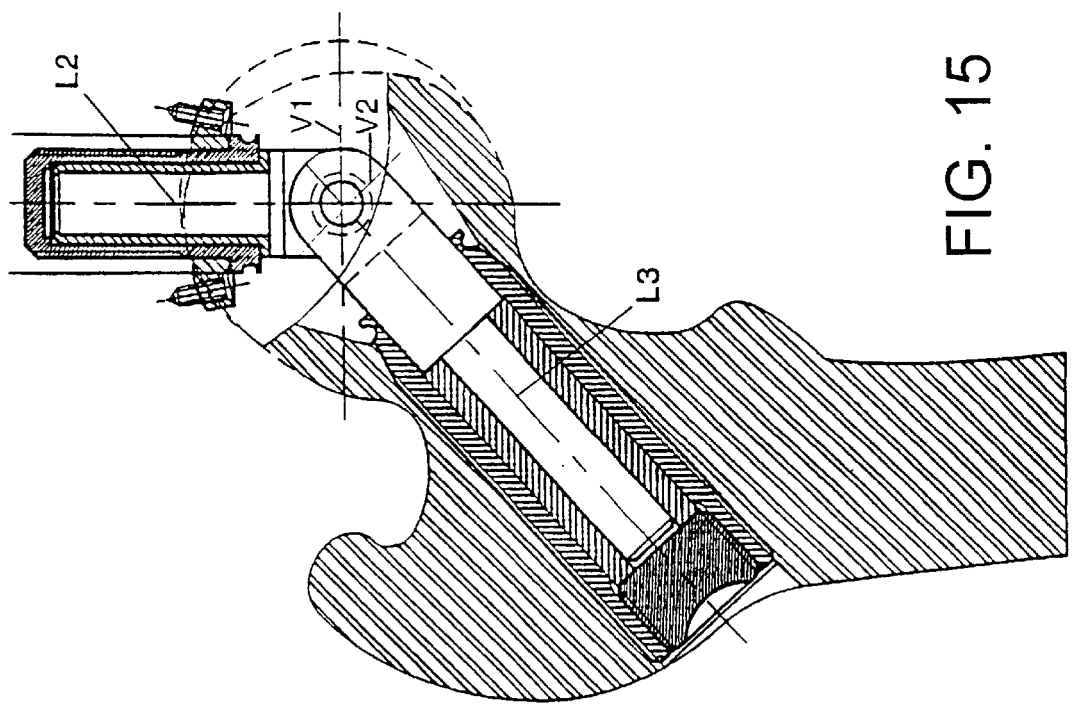
FIG. 15 is a similar view as presented in FIG. 14, with the orientation of the femur relative to the hip bone being normal.
Figure 14:
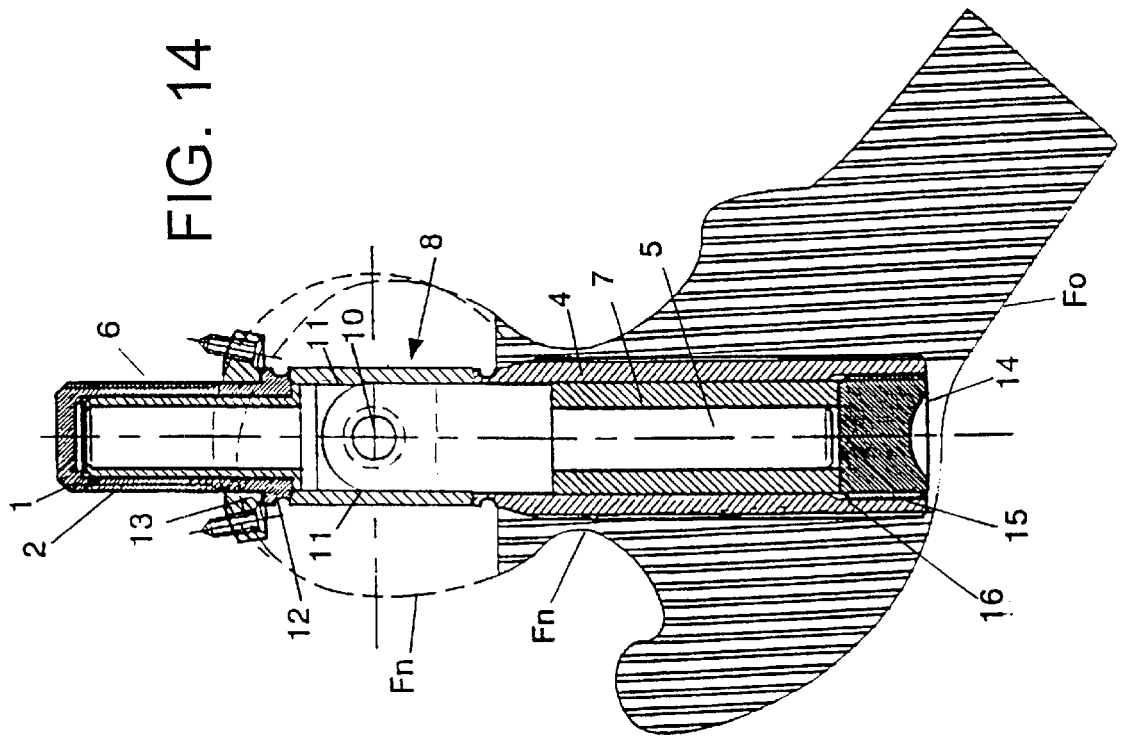
FIG. 14 shows the different parts of the hip prosthesis in mounted condition, with the femur being in an unnatural position relative to the hip bone.

In FIG. 13, the hip bone bush 1 has been arranged in the end position. The hip bone bush 1 can have its outer circumference provided with a coarse screw thread engaging the hip bone A, or can be secured in the hip bone by means of cement, resin or like means, The flange 12 of the hip bone bush 1 abuts against the supporting ring 13. Moroever, the outer circumference of the bush 1 fits tightly in the opening bounded by the supporting ring 13. In this manner, a proper distribution of the forces exerted by the hip bone bush 1 on the hip bone A is obtained. Then, the part 2,5,8, shown at the right-hand bottom of FIG. 13, can be inserted into the hip bone bush 1, while the hip bone pin 2, with the lining 6 surrounding this pin 2, is received In the hip bone bush 1. The pivot 8 is located in the joint cavity C, and the femoral pin 5, with the lining 7 surrounding this femoral pin, extends in the femoral bore 9. Then, the guide tube 19 can be pulled away from the femoral bore, after which the femoral bush 4 can be secured in the femoral bore. For this purpose, the femoral bush 4 can have its outside provided with screw thread or can be fixed in the femoral bore 9 by other fixation means, such as, for instance, cement or resin. Then, the locking plug 14 can be screwed down in the femoral bush 4 so as to fix the femoral pin 5 with the lining 7 associated therewith in axial direction relative to the femoral bush 4. For this purpose, the locking plug 14 has its outer surface provided with screw thread 15 engaging internal screw thread 16 provided in the femoral bush 4. As is shown in flogs. 6 and 14, the pivot 8 of the hip prosthesis can be surrounded by a sleeve 11 preventing ingrowth of bone or connective tissue in the pivot Finally, the leg B is brought into the normal position again, as shown in FIG. 15, and the incision can be closed.

For mounting the hip prosthesis according to the second alternative embodiment, the hip bone bore 3 and the femoral bore 9 are provided with internal screw thread after which the hip bone pin 202 comprising screw thread 203 is screwed in the hip bone bore 3 and the femoral pin 205 is screwed in the femoral bore 9. To facilitate the screw operation of the hip pin 202 and the femoral pin 205, these pins may be provided with engaging means 211 for tools. In the embodiment shown in FIG. 17 these engaging means are formed by a hexagonal profile on the end face of the femoral pin 205. The hip pin could be provided with an internal hexagonal socket which is fit for cooperation with a socket head wrench. FIG. 18 shows the second embodiment in mounted condition.

It is understood that with the above-described hip prosthesis and the method for fitting such hip prosthesis, the hip joint can be repaired with particularly little damage to tissue. It is readily understood that the invention is not limited to the above-described exemplary embodiment of the hip prosthesis and the method for the fitting thereof. Other pivot constructions or other types of the hip bone pins and the femoral pin are also possible. For instance, the pins could be of prismatic rather than cylindrical design, while the rotation of the pins relative to each other is obtained through one or more interposed bearings. It is essential that all parts of the hip prosthesis are so small that they can be brought into the intended final position via a bore in the femur.

What is claimed is:

1. A method for fitting a hip prosthesis, said prosthesis comprising a first fastening assembly intended for mounting on a hip bone and a second fastening assembly intended for mounting in the upper extremity of a femur, wherein the first and the second fastening assemblies are interconnected by a pivotable connection, and all parts of the hip prosthesis are sufficiently small and slender that they are each arrangeable in their intended positions in the hip bone and femur through a femoral bore in the femur, said femoral bore extending from the outside of the femur through the femoral neck to the femoral head substantially in the direction of the longitudinal central axis of the femoral neck;

said method comprising the steps of making a small incision in a leg to gain access to the top part of the femur, making said femoral bore in the femur, removing the femoral head via the femoral bore, making a hip bone bore in the hip bone at the location of the acetabulum via the femoral bore, mounting the first fastening assembly in the hip bone bore via the femoral bore, mounting the second fastening assembly in the femoral bore, and closing the incision.

2. A method according to claim 1, wherein the pivotal connection between the first fastening assembly and the second fastening assembly is a ball and socket assembly of which the external dimensions are smaller than the largest external dimension of the second fastening assembly.

3. A method according to claim 1, wherein the first fastening assembly comprises a hip pin having an external screw thread for engaging the hip bone and the second fastening assembly comprises a femoral pin having an external screw thread for engaging the femoral bone.

4. A method according to claim 1, comprising providing, during the fitting of the hip prosthesis, each of the hip bone bore and the femoral bore with an internal screw thread for the purpose of mounting the first and the second fastening assemblies.

5. A method for fitting a joint prosthesis, wherein the joint prosthesis comprises a first fastening assembly intended for mounting in a first bone and a second fastening assembly intended for mounting in a second bone and wherein the first and second fastening assemblies are interconnected by means of a pivotable connection and all parts of the prosthesis are sufficiently small and slender that they are each arrangeable in their intended positions in the first and second bones via a bore in the second bone;

said method comprising making a small incision to gain access to the second bone, making the bore in the second bone, removing a head of the second bone via the bore, mounting the first fastening assembly in the first bone via the bore, mounting the second fastening assembly in the bore and;

closing the incision.

* * * * *